United States Patent
Griffin

(10) Patent No.: US 10,668,222 B2
(45) Date of Patent: Jun. 2, 2020

(54) ASSEMBLY FOR A DRUG DELIVERY DEVICE AND DRUG DELIVERY DEVICE

(71) Applicant: Sanofi, Paris (FR)

(72) Inventor: Paul Roger Griffin, Warwick (GB)

(73) Assignee: Sanofi, Paris (FR)

( * ) Notice: Subject to any disclaimer, the term of this patent is extended or adjusted under 35 U.S.C. 154(b) by 425 days.

(21) Appl. No.: 15/534,032

(22) PCT Filed: Dec. 10, 2015

(86) PCT No.: PCT/EP2015/079304
§ 371 (c)(1),
(2) Date: Jun. 8, 2017

(87) PCT Pub. No.: WO2016/092037
PCT Pub. Date: Jun. 16, 2016

(65) Prior Publication Data
US 2017/0326304 A1    Nov. 16, 2017

(30) Foreign Application Priority Data

Dec. 10, 2014  (EP) ..................................... 14306993

(51) Int. Cl.
*A61M 5/315*       (2006.01)

(52) U.S. Cl.
CPC ...... *A61M 5/31551* (2013.01); *A61M 5/3155* (2013.01); *A61M 5/31533* (2013.01);
(Continued)

(58) Field of Classification Search
CPC .............. A61M 5/315; A61M 5/31536; A61M 5/31535; A61M 5/31545; A61M 5/31548;
(Continued)

(56) References Cited

U.S. PATENT DOCUMENTS

2012/0165751 A1*  6/2012  Plumptre .......... A61M 5/31551
604/207

FOREIGN PATENT DOCUMENTS

| CN | 102458535 | 5/2012 |
| JP | 2012-528633 | 11/2012 |

(Continued)

OTHER PUBLICATIONS

International Preliminary Report on Patentability in International Application No. PCT/EP2015/079304, dated Jun. 13, 2017, 6 pages.
(Continued)

*Primary Examiner* — Jason E Flick
(74) *Attorney, Agent, or Firm* — Fish & Richardson P.C.

(57) ABSTRACT

An assembly for a drug delivery device is provided comprising a screw member comprising a thread, the thread including at least two consecutive portions, the portions having different leads. The device further includes a nut member. The assembly is configured such that, in a first portion of the thread, the nut member includes a first position with respect to an axis transversal to the rotational axis and in a second portion of the thread, the nut member includes a second position with respect to the axis transversal to the rotational axis. The nut member is configured to perform a tilting movement from the first position into the second position when the nut member passes from the first portion to the second portion. Furthermore, a drug delivery device comprising the assembly is described.

20 Claims, 3 Drawing Sheets
Specification includes a Sequence Listing.

(52) U.S. Cl.
 CPC .... *A61M 5/31541* (2013.01); *A61M 5/31583* (2013.01); *A61M 5/31585* (2013.01)
(58) Field of Classification Search
 CPC .......... A61M 5/31565; A61M 5/31576; A61M 5/31533; A61M 5/31541; A61M 5/3155; A61M 5/31551; A61M 5/31583; A61M 5/31585
 USPC ....................................................... 604/211
 See application file for complete search history.

(56) References Cited

FOREIGN PATENT DOCUMENTS

| WO | WO 2008/058666 | 5/2008 |
|----|----------------|--------|
| WO | WO 2010/139645 | 12/2010 |

OTHER PUBLICATIONS

International Search Report and Written Opinion in International Application No. PCT/EP2015/079304, dated Feb. 11, 2016, 8 pages.

\* cited by examiner

Fig. 6a
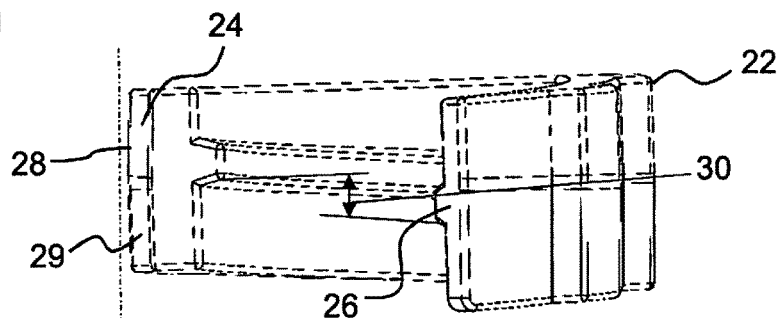
Fig. 6b
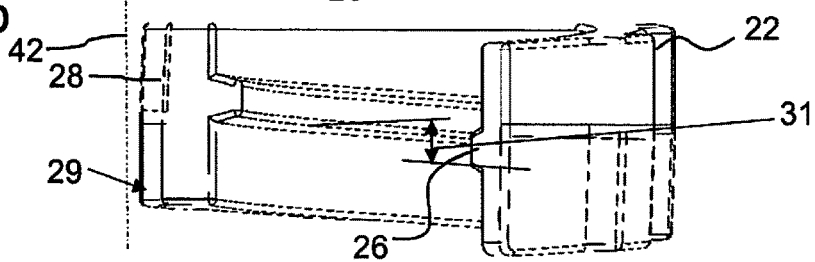
Fig. 7a
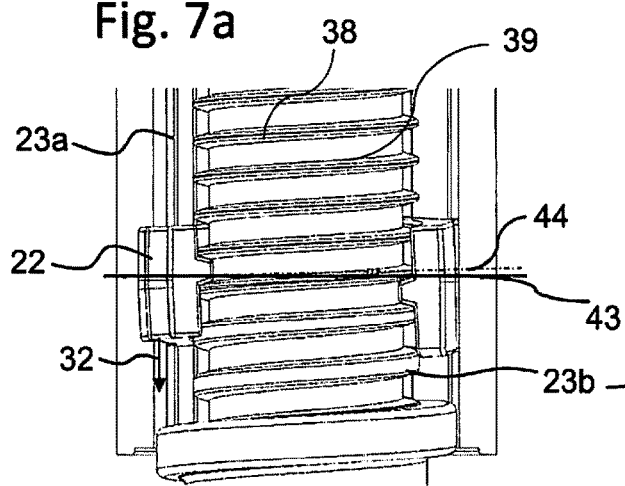
Fig. 7b
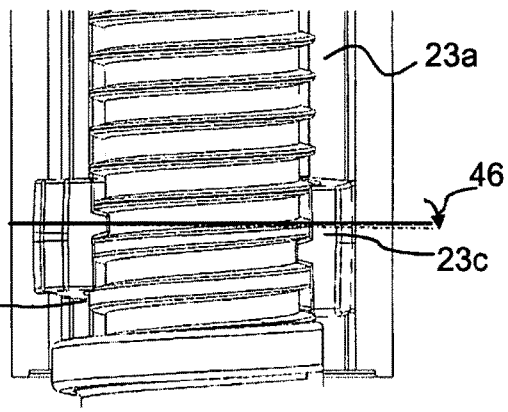
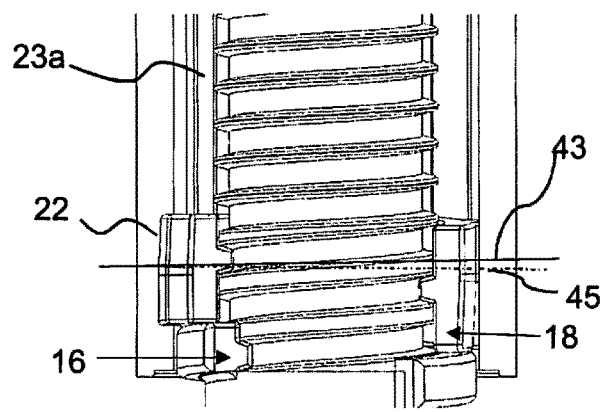
Fig. 7c
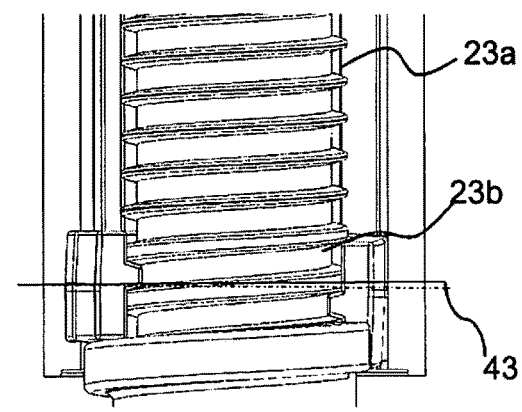
Fig. 7d

ASSEMBLY FOR A DRUG DELIVERY DEVICE AND DRUG DELIVERY DEVICE

CROSS-REFERENCE TO RELATED APPLICATIONS

This application is a U.S. national stage application under 35 USC § 371 of International Application No. PCT/EP2015/079304, filed on Dec. 10, 2015, which claims priority to European Patent Application No. 14306993.8, filed on Dec. 10, 2014, the entire contents of which are incorporated herein by reference.

TECHNICAL FIELD

The present disclosure relates to an assembly for a drug delivery device. Furthermore, the present disclosure relates to a drug delivery device.

BACKGROUND

In a drug delivery device, often, a bung within a cartridge containing a plurality of doses of a drug is displaced by a shaft. Thereby, a dose of the drug is expelled from the cartridge.

A drug delivery device is described in document WO 2008/058666 A1, for example.

SUMMARY

In certain aspects, an improved drug delivery device is provided.

One aspect relates to an assembly for a drug delivery device. The assembly may comprise a shape and/or outer dimension to be integrated into the drug delivery device. Furthermore, the assembly may be produced and assembled under sterile conditions as to be suited for being integrated in the device. The assembly comprises a screw member. The screw member may be shaped sleeve-like. The screw member may comprise an elongated shape. The screw member comprises a thread. The thread may be arranged on an outer surface of the screw member. The thread may be arranged along the screw member. The thread may comprise at least two consecutive portions. Preferably, the thread comprises exactly two consecutive portions. In other words, the thread may comprise a first portion and a second portion. The consecutive portions may be adapted and arranged to merge into one another. The thread may comprise a transition region wherein the consecutive portions merge into one another. The two consecutive portions have different leads.

The assembly further comprises a nut member. The nut member may be a half-nut or a ring-shaped full nut. The nut member and the screw member are adapted and arranged to be rotated with respect to one another about a rotational axis during a dose setting operation of the assembly. During the relative rotation, the nut member is axially displaced along the screw member from a start position to an end position with respect to the screw member due to mechanical cooperation of the nut member with the thread. During the relative rotation, the nut member is engaged with the thread of the screw member and passes along the thread towards the end position. The configuration and mechanical cooperation of the components of the assembly may help to facilitate provision of a safe device. In particular, the nut member may be designed as a last dose nut which prevents setting a dose that is higher than the amount of a drug remaining in the drug delivery device. Such a nut member may prevent a user from receiving an under-dose of the drug if the device is empty before the set dose is delivered. Thereby, the safety of the device is improved.

The assembly may be configured such that, the nut member performs a tilting movement when the nut member passes from being engaged with a first portion of the thread to being engaged with the second portion of the thread.

In the first portion of the thread, an axis of nut member may be at a first angle relative to the rotational axis, and in a second portion of the thread, the axis of nut member may be at a second angle relative to the rotational axis. This may force the nut member to perform the tilting movement from the first angle to the second angle when the nut member passes from the first portion to the second portion. The axis of the nut member may an axis which is defined by a straight line connecting of two points on opposite sides of an outer surface of the nut member.

In the first portion, the nut member may be in a first position with respect to an axis transversal to the rotational axis. In other words, when the nut member is engaged with the first portion, it may enclose a first angle with the axis transversal to the rotational axis. In the second portion, the nut member may comprise a second position with respect to the axis transversal to the rotational axis. In other words, when the nut member is engaged with the second portion, it may enclose a second angle with the axis transversal to the rotational axis. The first angle may be different from the second angle. The nut member may be configured to perform a tilting movement from the first position into the second position when the nut member passes from the first portion to the second portion. When the nut member has passed from the first portion into the second portion, the tilting movement may have been performed completely. By means of the tilting movement, the nut member may accommodate to the different leads of the consecutive portions. In this way, provision of a reliable and flexible drug delivery device is facilitated.

According to one embodiment, the nut member comprises at least one interface feature. Preferably, the nut member comprises exactly one interface feature. The interface feature is adapted and arranged to mechanically cooperate with the thread, in particular with the different portions of the thread. In at least one of the portions of the thread, the interface feature mechanically cooperates with the thread via distinct and separated contact points, e.g. via one, two, three or more contact points. In particular, in at least one portion, the interface feature may not be in full face contact with the portion when engaging the portion. Preferably, the interface feature mechanically cooperates via distinct and separated contact points, preferably three contact points, when being engaged with the first portion. This may allow the nut member to engage with thread portions having different leads. The nut member may perform a rotation off the rotational axis when being engaged with the first portion. The rotation off the rotational axis may be in the anti-clockwise direction.

The interface feature may comprise at least a partial turn of a thread. In particular, the interface feature may comprise a half turn or a full turn.

According to a further embodiment, the assembly further comprises a cartridge. The cartridge may contain at least one, preferably a plurality of doses of a drug. The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);
or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(o)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, -continued H-(Lys)6-desPro36, Pro37, Pro38 [Met(O)14,
Asp28] Exendin-4(1-39)-NH2, H-Asn-(Glu)5-des Pro36, Pro37, Pro38 [Met(O)14,
Asp28] Exendin-4(1-39)-NH2, des Pro36, Pro37, Pro38 [Met(O)14, Asp28]
Exendin-4(1-39)-(Lys)6-NH2, H-(Lys)6-des Pro36, Pro37, Pro38 [Met(O)14,
Asp28] Exendin-4(1-39)-(Lys)6-NH2, H-Asn-(Glu)5 des Pro36, Pro37, Pro38 [Met(O)14,
Asp28] Exendin-4(1-39)-(Lys)6-NH2, H-Lys6-des Pro36 [Met(O)14, Trp(O2)25, Asp28]
Exendin-4(1-39)-Lys6-NH2, H-des Asp28 Pro36, Pro37, Pro38 [Met(O)14,
Trp(O2)25] Exendin-4(1-39)-NH2, H-(Lys)6-des Pro36, Pro37, Pro38 [Met(O)14,
Asp28] Exendin-4(1-39)-NH2, H-Asn-(Glu)5-des Pro36, Pro37, Pro38 [Met(O)14,
Trp(O2)25, Asp28] Exendin-4(1-39)-NH2, des Pro36, Pro37, Pro38 [Met(O)14, Trp(O2)25,
Asp28] Exendin-4(1-39)-(Lys)6-NH2, H-(Lys)6-des Pro36, Pro37, Pro38 [Met(O)14,
Trp(O2)25, Asp28] Exendin-4(S1-39)-(Lys)6-NH2, H-Asn-(Glu)5-des Pro36, Pro37, Pro38 [Met(O)14,
Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The assembly further comprises a dosing mechanism. The dosing mechanism is operable for setting and delivering a dose of the drug from the cartridge. The dosing mechanism comprises a last dose stop mechanism. The last dose stop mechanism is adapted and arranged to prevent a user from setting a dose of the drug which exceeds a remaining amount of drug in the cartridge. The last dose stop mechanism comprises at least one stop feature. The stop feature is provided by the screw member. The stop feature may be provided at an end portion of the thread. The stop feature may comprise a protrusion or a lug, for example. The last dose stop mechanism further comprises at least one interaction feature. The interaction feature is provided by the nut member. The interaction feature may comprise a protrusion, for example. The stop feature and the interaction feature are configured to mechanically cooperate with one another when the nut member is in the end position with respect to the screw member such that further relative rotation of the nut member and the screw member for axially displacing the nut member away from the start position is prevented. In other words, the end position of the nut member with respect to the screw member is defined by mechanical cooperation of the stop feature and the interaction feature. The displacement distance of the nut member between the start position and the end position may correspond to the amount of drug contained in the cartridge.

By means of the last dose stop mechanism the dose of drug that may be set by a user is limited to less than or equal to the amount of drug remaining in the cartridge. This has the advantage that the user knows how much will be delivered before starting dose delivery. It also ensures that dose delivery stops in a controlled manner without the bung entering the neck portion of the cartridge where the diameter is smaller which may result in an underdose. In this way, setting or dispensing of an underdose of the drug is prevented. Thus, safety of the device is increased.

According to a further embodiment, the assembly and/or the device comprise a distal end and a proximal end. The distal end may be arranged at a dispensing end of the device. The start position of the nut member may be arranged closer to the distal end than the end position. Alternatively, the start position of the nut member may be arranged closer to the proximal end than the end position. The thread comprises the previously mentioned first portion and the second portion. The first portion may be arranged closer to the distal end than the second portion. The lead of the first portion may be less than the lead of the second portion. The first portion may be a slow thread and the second portion may be a fast thread. The ratio between slow and fast thread leads may be 1:1.5, for example. Other ratios between the slow and fast thread leads are possible, e.g. 1:2 or 1:2.5. In particular, the ratio may be in the range of 1:1.2 to 1:2.5, preferably in the range of 1:1.4 to 1:2.

The interface feature may comprise a single protrusion. In particular, the interface feature may comprise a partial turn of a thread. The specific shape of the interface feature may allow the nut member to mesh with the variable thread, i.e. the first and the second portion of the thread, of the screw member without interference. In an alternative design, the interface feature may comprise a full turn of a thread. This design also allows the interface feature to mesh with the variable thread. In this case, enough clearance should be provided between the interface feature and the thread.

The lead of the interface feature may be similar or equal to the fast thread form of the screw member. In other words, the lead of the interface feature may be similar or equal to the lead of the second portion. Preferably, the lead of the interface feature is equal to the lead of the second portion. In this way, a surface engagement between the interface feature and the second portion may be increased as compared to a surface engagement between the interface feature and the first portion. Thus, a higher axial load may be enabled to be restrained when the nut member mechanically cooperates with the second portion. However, a load may occur mostly torsional, thereby avoiding transfer of the load through the thread.

According to a further embodiment, the interface feature comprises a distal face and a proximal face. The proximal face may be arranged closer to the stop feature of the screw member than the distal face. The distal face may be closer to the cartridge than the proximal face. The respective faces are configured to mechanically cooperate with a distal and a proximal wall of a winding of the thread. When the nut member mechanically cooperates with the first portion, the distal face may be configured to be in at least two-point contact, e.g. in three-point contact, with the distal wall of a winding of the first portion. When the nut member mechanically cooperates with the first portion, the proximal face may be configured to be in at least two-point contact, e.g. in three-point contact, with the proximal wall of the respective winding of the first portion.

When the nut member mechanically cooperates with the second portion, the distal and proximal faces may be configured to have a greater contact area with the distal and proximal wall of a winding of the second portion compared to the contact area of the distal and proximal faces with the distal and proximal wall of a winding of the first portion when the nut member mechanically cooperates with the first portion.

In other words, when the nut member mechanically cooperates with the second portion, the distal and/or proximal faces are configured to have a greater contact area with the distal and/or proximal wall of a winding of the second portion than when mechanically cooperating with the first portion. Preferably, when the nut member mechanically cooperates with the second portion, the distal face may be in full-face contact with the distal wall of a winding of the second portion. When the nut member mechanically cooperates with the second portion, the proximal face may be in full-face contact with the proximal wall of the corresponding winding of the second portion. Accordingly, in the first portion, rotation of the nut member and the screw member with respect to one another may be facilitated by means of minimized contact areas. In the second portion, contact stresses are minimized by means of increased contact areas.

According to a further embodiment, the assembly comprises a housing. The housing may be an exterior housing of the device. The housing may form an outer surface of the device. The housing may be adapted and arranged for protecting further components of the device from environmental influences. The assembly may further comprise an inner housing sleeve. The inner housing sleeve may be arranged within the housing. The housing and the inner housing sleeve may be separate components. The inner housing sleeve may be inserted into the housing. The inner housing sleeve may be connected, preferably non-releasably connected to the housing. The inner housing sleeve may be prevented from rotation with respect to the housing. In this case, the inner housing sleeve may be glued to the housing, for example. Alternatively, the inner housing sleeve may be rotatable with respect to the housing. In this case, the inner housing sleeve may comprise a projection and the housing may comprise a groove, for example, for rotatably connecting the inner housing sleeve to the housing. The inner housing sleeve may be prevented from axial movement with respect to the housing.

The inner housing sleeve may comprise at least one first splining member, e.g. a protrusion or a groove. The inner housing sleeve may comprise a plurality of first splining members, e.g. two, three or more first splining members. The first splining member may be arranged on an inner surface of the inner housing sleeve. The first splining member may extend along the inner surface of the inner housing sleeve.

The nut member may comprise at least one second splining member, e.g. a protrusion. The nut member may comprise a plurality of second splining members, e.g. two, three or more second splining members. The nut member may be splined to the inner housing sleeve due to mechanical cooperation of the splining members. Hence, a direct mechanical connection or contact between the nut member and the housing may be prevented. In this way, the nut member or the screw member may be designed to be rotated during a dose setting operation depending on the specific embodiment of the inner housing sleeve.

The splined connection between the nut member and the inner housing sleeve may be relieved for enabling the tilting movement from the first position into the second position when the nut member passes from the first portion to the second portion. The splined connection between the nut member and the inner housing sleeve may be relieved for enabling a rotational movement off the rotational axis e.g. in the anti-clockwise direction when the nut member is engaged with the first portion.

For enabling the tilting movement when the nut member passes from the first position to the second position, the interface feature of the nut member and the windings of the portions may be adapted such that, in at least one portion, preferably the first portion, there is play between the interface feature and the walls of the windings. When being engaged with the first portion, the nut member may be rotatable off the rotational axis relative to the first splining member due to the specific shaping of the splining members, the windings and the interface feature.

According to one embodiment, at least one of the splining members may be at least partly angled or curved away from the rotational axis. In other words, the at least one of the splining members may at least partly run obliquely with respect to an axis parallel to the rotational axis. Preferably, the second splining member is at least partly angled or curved. The second splining member may comprise at least in parts an angled or rounded outer shape, in particular an angled or rounded outer surface. The second splining member may, thus, only in parts, be arranged parallel to the rotational axis when the nut member is engaged with the screw member. In other words, only parts of the outer surface of the second splining member may be in direct mechanical contact with a corresponding surface of the first splining member. Thus, the tilting movement from the first position into the second position when the nut member passes from the first portion to the second portion is enabled.

In particular, the second splining member may comprise an outer shape having a first part and a second part wherein the first part is inclined relative to the second part. The second splining member may comprise multiple splines wherein the respective first part may be a distal part and the respective second part may be a proximal part in a one of the splines and wherein the respective first part may be a proximal part and the respective second part may be a distal part in another one of the splines. Further, in another spline, the respective first part may be a middle part arranged between two respective second parts which are arranged at a proximal end and a distal end of the spline.

The second part of the second splining member may run obliquely with respect to the rotational axis when the nut member is in the first position. In other words, the second part may be relieved from the first splining member when the nut member is engaged with the first portion. The second part of the second splining member may be oblique with respect to the rotational axis when the nut member is engaged with the first portion. The second part part may be more oblique relative to the rotational axis than the first part when the nut member is engaged with the first portion.

The second part of the second splining member may run less obliquely to the rotational axis than the first part when the nut member is in the second position. The second part may run parallel to the rotational axis when the nut member is in the second position. The second part may be fully engaged with the first splining member when the nut member mechanically cooperates with the second portion. The second part part may be less oblique relative to the rotational axis than the first part when the nut member is engaged with the second portion.

According to a further embodiment, during a dose setting operation, the screw member is rotated with respect to the nut member and to the inner housing sleeve. The inner housing sleeve may be prevented from rotation due to mechanical cooperation with the housing and the nut member may be prevented from rotation due to mechanical cooperation with the inner housing sleeve, e.g. by a splined connection. In this way, relative rotational movement of the screw member and the nut member causes the nut member to follow the thread on the screw member and so displace axially towards the end position.

According to a further embodiment, during a dose setting operation, the inner housing sleeve and the nut member are rotated with respect to the screw member. The screw member may be prevented from rotation due to mechanical cooperation with the housing. The nut member may be rotated due to mechanical cooperation with the inner housing sleeve. In this way, relative rotational movement of the screw member and the nut member for axially displacing the nut member towards the end position is enabled.

According to a further embodiment, during a dose delivery operation, the screw member, the inner housing sleeve and the nut member are prevented from rotation with respect to one another such that the nut member is prevented from axial movement with respect to the screw member. In particular, during the dose delivery operation, relative rotation between the nut member and the screw member may be prevented.

According to a further embodiment, during a dose delivery operation, the screw member and the inner housing sleeve rotate together with respect to the housing due to mechanical cooperation with one another such that the nut member is prevented from axial movement with respect to the screw member.

A further aspect relates to a drug delivery device. The drug delivery device comprises the previously described assembly. The assembly may be integrated in the device. In this way, a very stable and safe device is provided.

Of course, features described above in connection with different aspects and embodiments may be combined with each other and with features described below.

BRIEF DESCRIPTION OF THE DRAWINGS

Further features and refinements become apparent from the following description of the exemplary embodiments in connection with the accompanying figures.

Like elements, elements of the same kind and identically acting elements may be provided with the same reference numerals in the figures.

DETAILED DESCRIPTION

Figure 1:
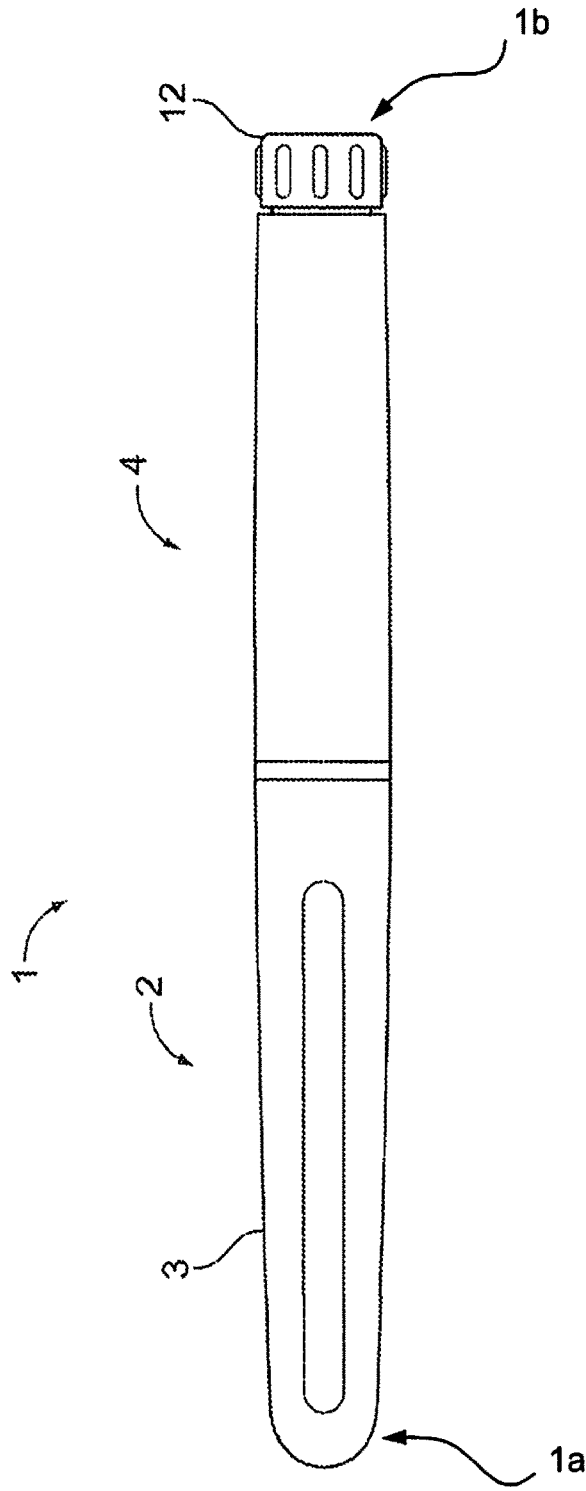
FIG. 1 schematically shows a side view of a drug delivery device.
Figure 2:
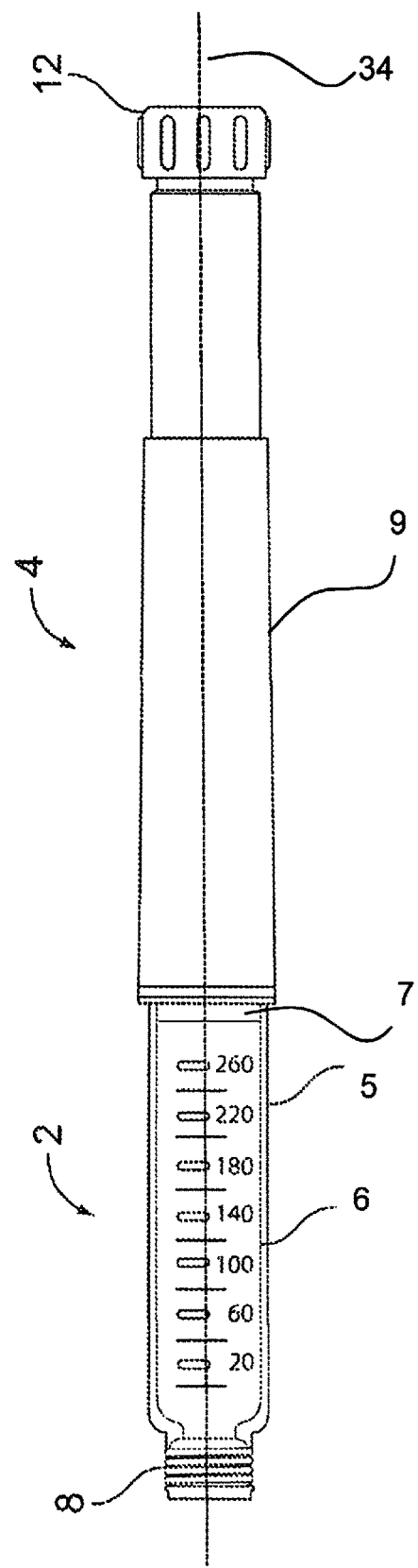
FIG. 2 schematically shows a side view of parts of the drug delivery device of FIG. 1, FIG. 3 schematically shows an exploded view of parts of the drug delivery device of FIG. 1, FIG. 4 schematically shows a side view of a part of the drug delivery device of FIG. 1, FIG. 5 schematically shows a side view of a part of the drug delivery device of FIG. 1, FIGS. 6a and 6b schematically show a side view of a part of the drug delivery device of FIG. 1, FIGS. 7a to 7d schematically show a partial section view of a part of the drug delivery device of FIG. 1.

In FIGS. 1 and 2 a drug delivery device 1 is shown. The drug delivery device 1 comprises dosing mechanism 4. The dosing mechanism 4 comprises a housing 9. The drug delivery device 1 and the housing 9 have a distal end 1a and a proximal end 1b. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end 1a and the proximal end 1b are spaced apart from one another in the direction of an axis. The axis may be the longitudinal axis or rotational axis 34 of the device 1.

The drug delivery device 1 comprises a cartridge retaining part 2. The cartridge retaining part 2 comprises a cartridge holder 5. The cartridge retaining part 2 comprises a cartridge 6. The cartridge 6 contains a drug, preferably a plurality of doses of the drug. The cartridge 6 is retained within the cartridge holder 5. The cartridge holder 5 stabilizes the position of the cartridge 6 mechanically. The cartridge holder 5 is connectable, e.g. by a threaded engagement, by a weld or by a snap-fit, to the housing 9. The cartridge holder 5 and the housing 9 may be releasably or irreleasably connected to one another.

A needle assembly (not explicitly shown) can be arranged at the distal end of the cartridge holder 5, e.g. by means of a thread 8. A cap 3 can be releasably secured to the drug delivery device 1 for protecting the device 1, and, in particular, the cartridge holder 5 or the cartridge 6 from environmental influences, e.g. when the device 1 is not used. A bung 7 is slideably retained within the cartridge 6. The bung 7 seals the cartridge 6 proximally. Movement of the bung 7 in the distal direction with respect to the cartridge 6 causes the drug to be dispensed from the cartridge 6.

The drug delivery device 1 may be a pen-type device, in particular a pen-type injector. The device 1 may be a re-usable device, which means that the cartridge 6 can be replaced, in particular during a reset operation, by a replacement cartridge for dispensing a plurality of doses from the replacement cartridge. Alternatively, the device 1 may be a disposable device 1 which means that the cartridge 6 is non-releasably connected to the cartridge holder 5.

The dosing mechanism 4 comprises a dose dial grip 12. For setting a dose of the drug, a user rotates the dose dial grip 12, which is described later on in detail.

FIGS. 3 to 7d schematically show parts of the drug delivery device 1. The dosing mechanism 4 comprises a screw member 23, a nut member 22 and an inner housing sleeve 10 (see FIG. 3).

The inner housing sleeve 10 comprises an insert of the housing 9. The inner housing sleeve 10 is secured against axial movement with respect to the housing 9 by mechanical cooperation with the housing 9. The inner housing sleeve 10 may be secured against rotational movement with respect to the housing 9 by mechanical cooperation with the housing 9, e.g. by a splined connection. Alternatively, the inner housing sleeve 10 may be rotatable with respect to the housing 9 at least for setting a dose. In particular, when the screw member 23 is rotatable with respect to the housing 9 during a dose setting operation, the inner housing sleeve 10 may be adapted to be non-rotatable with respect to the housing 9 during the dose setting operation and vice versa.

The nut member 22 is shaped like a half-sleeve. The nut member 22 may comprise a partial nut or half-nut (see FIGS. 3 and 5). The nut member 22 comprises an axial dimension smaller than the axial dimension of the inner housing sleeve 10. The nut member 22 is arranged within the inner housing sleeve 10. The nut member 22 is arranged at least partly around the screw member 23. As the nut member 22 is a half-nut, it is assembled onto the screw member 23 from the radial direction. Alternatively, the nut member 22 may be assembled axially in the proximal direction.

The nut member 22 is secured against rotation around the rotational axis 34 with respect to the inner housing sleeve 10 by mechanical cooperation with the inner housing sleeve 10. Preferably, the nut member 22 is splined to the inner housing sleeve 10. For this purpose, the inner housing sleeve 10 comprises a plurality of first splining members 40, e.g. grooves (see FIG. 3). The respective groove 40 extends along an inner surface of the inner housing sleeve 10. The nut member 22 comprises several second splining members 24, e.g. lugs or protrusions (see FIG. 5). The respective protrusion 24 is arranged on an outer surface of the nut member 22. The protrusion 24 protrudes from the nut member 22 in the radial outward direction. The protrusion 24 extends along the nut member 22. The protrusion 24 comprises a first part 28 and a second part 29 (see FIGS. 6a and 6b). Alternatively, the inner housing sleeve 10 may comprise protrusions and the nut member 22 may comprise grooves (not explicitly shown). The splined connection between the nut member 22 and the inner housing sleeve 10 can be relieved. In this way, the nut member 22 is, under certain circumstances, rotatable off the rotational axis 34 relative to the first splining member 40 and, thus, to the inner housing sleeve 10, which is explained later on in detail.

The nut member 22 and the screw member 23 are rotatable with respect to one another about the rotational axis 34 during a dose setting operation. The nut member 22 is axially moveable with respect to the inner housing sleeve 10 due to mechanical cooperation of the first and second splining member 24, 40.

The screw member 23 is arranged within the inner housing sleeve 10. The screw member 23 is arranged at least partly within the nut member 22. The screw member 23 may be formed sleeve-like. The screw member 23 may comprise a shaft at its distal end (not explicitly shown) for driving the bung 7 in the distal direction with respect to the housing 9. Alternatively, a separate part may push the bung. In particular, the assembly may comprise a piston rod (not shown) which is splined to the screw member 29 and threaded to the housing 9. The assembly may be configured such that when the screw member 23 rotates, the piston rod advances and, thereby, drives the bung in the distal direction.

The screw member 23 may be rotatable with respect to the housing 9. Alternatively, the screw member 23 may be prevented from rotation with respect to the housing 9, e.g. by means of a splined connection with the housing 9.

The dosing mechanism 4 further comprises a last dose stop mechanism which prevents a user from setting a dose of the drug which exceeds a remaining amount of drug in the cartridge 6. The last dose stop mechanism comprises a stop feature 16 (see FIG. 4). The stop feature 16 is provided by the screw member 23. The stop feature 16 is arranged in a proximal end portion of the screw member 23. The stop feature 16 may be an edge or a protrusion. The stop feature 16 may protrude from the screw member 23 in a radial direction. The last dose stop mechanism further comprises an interaction feature 18. The interaction feature 18 is provided by the nut member 22 (see FIG. 7c). The interaction feature 18 may comprise an edge or a protrusion protruding from the nut member 22 in a radial direction.

The stop feature 16 and the interaction feature 18 are configured to mechanically cooperate with one another when the nut member 22 is in an end position or proximal position with respect to the screw member 13 such that further relative rotation of the nut member 22 and the screw member 23 for axially displacing the nut member 22 away from the start position is prevented. Hence, mechanical cooperation of the stop feature 16 and the interaction feature 18 determines the end end position of the nut member 22 with respect to the screw member 23. The length of the axial travel of the nut member 22 on the screw member 23 corresponds to the maximum number of doses of the drug which can be dispensed from the device 1.

When the nut member 22 has reached the end position, a rotational abutment is created by means of mechanical cooperation of the stop feature 16 and the interaction feature 18, coupling the screw member 23 to the inner housing sleeve 10. Accordingly, in the end position, relative rotation between the screw member 23 and the inner housing sleeve 10 leading to axial movement of the nut member 22 in the proximal direction, is no longer possible. However, the nut member 22 may be enabled to travel in the distal direction back towards the start position, e.g. for a dose correction operation.

Figure 3:
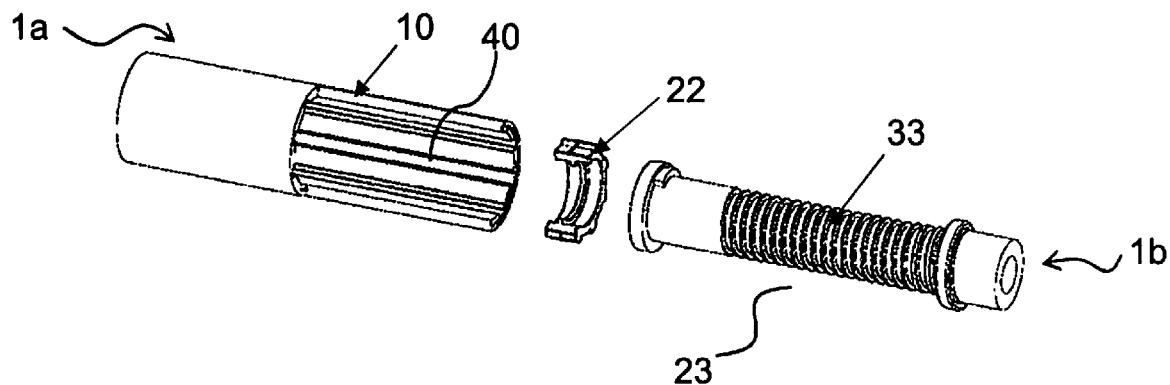
Figure 4:
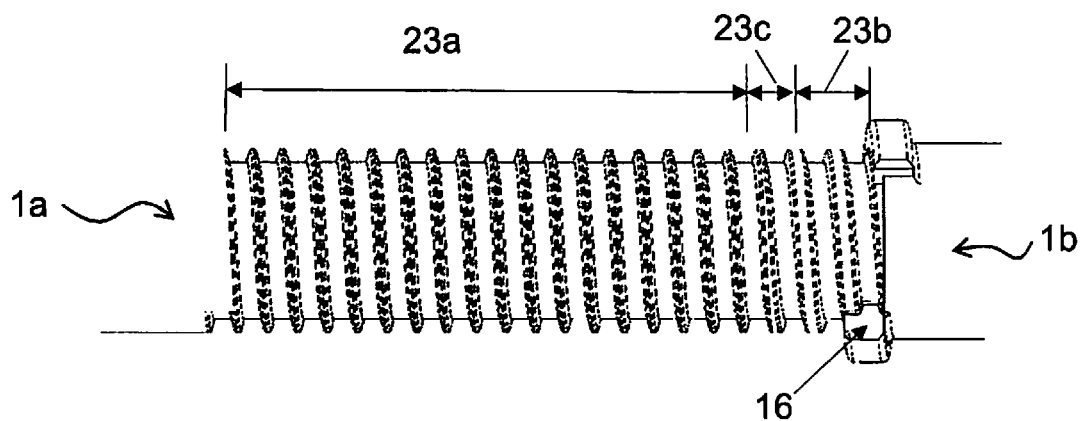

The screw member 23 comprises a helical thread 33 (see FIGS. 3 and 4). The thread 33 is arranged on an outer surface of the screw member 23. In an alternative design, the thread 33 may be arranged on an inner surface of the screw member 33. In this case, the screw member 23 may be arranged such that the inner housing sleeve is arranged inside the screw member 23.

The thread 33 comprises two consecutive portions, i.e. a first portion 23a and a second portion 23b. Alternatively, the thread 33 may comprise three or more consecutive portions (not explicitly shown). A transition region may be arranged between each of the consecutive portions wherein the transition region is significantly smaller than the respective portions.

The first portion 23a is arranged in a distal portion of the screw member 23. The second portion 23b is arranged more proximally than the first portion 23a. The first portion 23a has a greater axial dimension than the second portion 23b. The thread 33 has a variable lead. The lead of the first portion 23a is less than the lead of the second portion 23b. The first portion 23a is a slow thread and the second portion 23b is a fast thread. The ratio between slow and fast thread leads is 1:1.5, for example. The first portion 23a is single-start thread, the second portion 23b is a twin-start thread.

Figure 5:
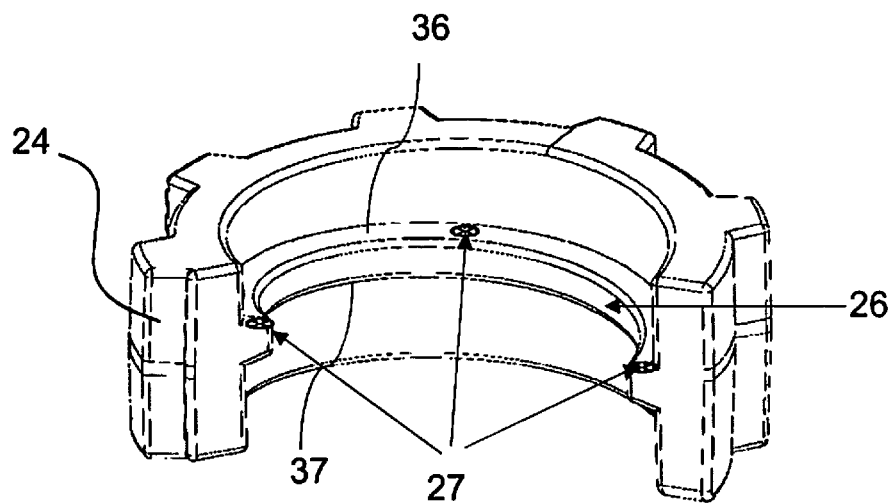

The nut member 22 mechanically cooperates with the screw member 23 and, in particular, with the thread 33 via one interface feature 26 (see FIG. 5). The interface feature 26 is arranged on an inner surface of the nut member 22. The interface feature 26 extends circumferentially along an outer surface of the nut member 22. The interface feature 26 comprises a partial turn of a thread. The lead of this partial turn is equal to the fast thread form of the screw member 23, i.e. it is equal to the lead of the second portion 23b. The specific shape of the interface fature 26 and increased clearances in the thread forms of the screw member 23 allow the nut member 22 to mesh with the different portions 23a, 23b without interference.

The splined engagement between the inner housing sleeve 10 and the nut member 22 and the mechanical cooperation of the interface feature 26 with the portions 23a, 23b enables a rocking movement of the nut member 22, i.e. a rotational movement off the rotational axis 34, as mentioned above when the nut member 22 travels towards the end position with respect to the screw member 23. For this purpose, the protrusion 24 comprises a rounded or angled outer shape, in particular an outer shape which is only in parts parallel to the rotational axis 34 when the nut member 22 is engaged with the screw member 23.

The second part 29 of the protrusion 24 is relieved from the inner housing sleeve 10 when the nut member 22 is engaged with the first portion 23a (see FIG. 6a). The second part 29 is oblique with respect to an axis 42 parallel to the rotational axis 34 when the nut member 22 is engaged with the first portion 23a. Accordingly, the nut member 22 is rotated anti-clockwise with respect to the inner housing sleeve 10 about an axis perpendicular to the rotational axis 34 when being engaged with the first portion 23a. Thus, when the nut member 22 is engaged with the first portion 23a, the nut member 22 is in a first position 44 with respect to an axis 43 perpendicular to the rotational axis 34 (see FIG. 7a). In other words, it encloses a first angle with the axis 43 perpendicular to the rotational axis 34. In particular, it is rotated anti-clockwise away from the axis 43 perpendicular to the rotational axis 34 (see FIG. 7a). The apparent lead is reduced when the nut member 22 is engaged with the first portion 23a as indicated by arrow 30 in FIG. 6a.

When the nut member 22 becomes engaged with the second portion 23b, the proximal portion 29 of the protrusion 24 becomes parallel with respect to the axis 42 (see FIG. 6b). Accordingly, the nut member 22 is rotatable clockwise off the rotational axis 34 with respect to the inner housing sleeve 10 when the nut member 22 passes into the second portion 23b. Thus, when the nut member 22 is engaged with the second portion 23b, the nut member 22 is in a second position 45 with respect to the axis 43 perpendicular to the rotational axis 34 (see FIG. 7c). In other words, it encloses a second angle with the axis 43 perpendicular to the rotational axis 34. In particular, it is rotated clockwise away from the axis 43 perpendicular to the rotational axis 34 during transition from the first portion 23a into the second portion 23b. The nut member 22 performs a tilting or rocking movement from the first position into the second position when the nut member 22 passes from the first portion 23a to the second portion 23b to accommodate the fast thread lead (see arrow 46 in FIG. 7b). When the nut member 22 is engaged with the fast thread, the half turn of the nut member 22 comprises a full fast thread lead as indicated by arrow 31 in FIG. 6b.

In the following, operation of the device 1 is described in detail:

After having assembled the device 1, the nut member 22 is positioned in a distal or start position with respect to the screw member 23 (not explicitly shown). In the start position, the nut member 22 mechanically cooperates with the first portion 23a as described above. Thus, in FIG. 7a, the interface feature 26 is engaged with a winding of the first portion 23a of the thread 33. The interface feature 26 comprises a distal face 36 and a proximal face 37 (see FIG. 5). The faces 36, 37 mechanically cooperate with a corresponding distal and proximal wall 38, 39 of a winding of the thread 33. When engaging the first portion 23a of the thread 33, the nut member 22 and, in particular, the interface feature 26, is in three-point contact with a winding of the first portion 23. This means, that the respective face 36, 37 mechanically cooperates via three distinct contact points 27 with the corresponding wall 38, 39 of the winding (see FIG. 5). The contact via the distinct contact points 27 occurs because the thread on the interface feature 26 does not match the thread 33 in the first portion 23a. To allow rotation even with a mismatched thread, clearance is increased.

For setting a dose, the dose dial grip is rotated 12. Rotation of the dose dial grip 12 is transferred into rotation of the screw member 23 due to mechanical cooperation with the dose dial grip 12 (not explicitly shown). The inner housing sleeve 10 is prevented from rotation due to the splined connection with the housing 9. Upon rotation of the screw member 23, the nut member 22 is axially displaced along the screw member 23 in the proximal direction from the distal position, i.e. the position in which the nut member 22 is located with respect to the screw member 23 after assembly of the device 1 was completed, to the previously mentioned proximal end position with respect to the screw member 23 due to mechanical cooperation of the nut member 22 with the thread 33.

Alternatively, for setting a dose, the dose dial grip is rotated 12. The inner housing sleeve 10 is rotated with respect to the screw member 23 due to mechanical cooperation with the dose dial grip 12 (not explicitly shown). In this case, the screw member 23 is prevented from rotation due to mechanical cooperation with the housing 9. The nut member 22 rotates together with the inner housing sleeve 10 due to the splined connection. Upon rotation of the inner housing sleeve 10 and the nut member 22, the nut member 22 is axially displaced along the screw member 23 in the proximal direction from the start position to the end position with respect to the screw member 23 due to mechanical cooperation of the nut member 11 with the thread 33.

In each embodiment, during a dose setting operation, the nut member 22 and the screw member 23 rotate with respect to one another.

According to one embodiment, during a dose delivery operation, the screw member 23, the inner housing sleeve 10 and the nut member 22 are prevented from rotation with respect to one another and with respect to the housing 9 such that the nut member 22 is prevented from axial movement with respect to the screw member 23. Rather, the screw member 23 and/or an associated shaft may move distally, thereby forcing the bung 7 in the distal direction with respect to the housing 9. In the alternative design wherein a piston rod is splined to the screw member 29 and threaded to the housing 9, the the piston rod is moved distally during the dose delivery operation, thereby forcing the bung 7 in the distal direction with respect to the housing 9.

Alternatively, for delivery of the dose, the screw member 23 and the inner housing sleeve 10 rotate together with respect to the housing 9 due to mechanical cooperation with one another. As the screw member 23 and the inner housing sleeve 10 rotate together at the same rate, no axial movement of the nut member 22 is generated. Rather, the screw member 23 may move distally, thereby forcing the bung 7 in the distal direction with respect to the housing 9. In an alternative design, the screw member 23 may move a piston rod distally, thereby forcing the bung 7 in the distal direction with respect to the housing 9.

When the nut member 22 moves towards the end position during subsequent dose setting operations, the nut member 22 mechanically cooperates with the different portions 23a, 23b of the thread 33. In particular, during subsequent dose setting operations, the nut member 22 moves proximally towards the end position (see arrow 32 in FIG. 7a), thereby entering a transition region 23c between the first portion 23a and the second portion 23b. While passing from the first portion 23a into the second portion 23b, the nut member 22 rotates clockwise to accommodate the increasing lead of the second portion 23b as shown in FIG. 7b.

When the nut member 22 engages the second portion 23b, the nut member 22 has completed its rocking movement and is arranged in the second position (see FIG. 7c). When engaging the second portion 23b, the contact area between distal and proximal faces 36, 37 and the corresponding wall 38, 39 of a winding of the second portion 23b is greater than when the nut member 22 engages the first portion 23a. In other words, when the nut member 22 transitions to the second portion 23b, the point contacts become a full face contact to minimise contact stresses when the last dose stop engages.

Upon further movement in the proximal direction, the nut member 22 reaches the end position with respect to the screw member 23, which is shown in FIG. 7d. In the end position, the interaction feature 18 of the nut member 22 mechanically cooperates with the stop feature 16 of the screw member as described above. Thus, further movement of the nut member 22 in the proximal direction is prevented. The last complete dose has been dispensed from the cartridge 6 and the cartridge 6 may be replaced by a replacement cartridge, for example.

Other implementations are within the scope of the following claims. Elements of different implementations may be combined to form implementations not specifically described herein.

REFERENCE NUMERALS

1 Drug delivery device
1a Distal end
1b Proximal end
2 Cartridge retaining part
3 Cap
4 Dosing mechanism
5 Cartridge holder
6 Cartridge 7 Bung
8 Thread
9 Housing
10 Inner housing sleeve
12 Dose dial grip
16 Stop feature
18 Interaction feature
22 Nut member
23 Screw member
23a First portion
23b Second portion
23c Transition region
24 Second splining member/protrusion
26 Interface feature
27 Contact point
28 first part
29 second part
30 Arrow
31 Arrow
32 Arrow
33 Thread
34 Rotational axis
36 Distal face
37 Proximal face
38 Distal wall
39 Proximal wall
40 First splining member/groove
42 Axis
43 Axis
44 First position
45 Second position
46 Arrow

The invention claimed is:

1. An assembly for a drug delivery device, the assembly comprising:
a screw member comprising a thread, the thread comprising at least two consecutive portions, the at least two consecutive portions having different leads; and
a nut member,
wherein the nut member and the screw member are adapted to be rotated with respect to one another about a rotational axis during a dose setting operation of the assembly, thereby axially displacing the nut member along the screw member from a start position to an end position with respect to the screw member due to mechanical cooperation of the nut member with the thread,
wherein the assembly is configured such that the nut member performs a tilting movement when the nut member passes from a first portion of the at least two consecutive portions to a second portion of the at least two consecutive portions, and
wherein when the nut member is engaged with the first portion, the nut member encloses a first angle with an axis transverse to the rotational axis, and when the nut member is engaged with the second portion, the nut member encloses a second angle with the axis transverse to the rotational axis, the second angle being different from the first angle.

2. The assembly according to claim 1, wherein:
the first portion of the thread is arranged distal to the second portion, and
a lead of the first portion is less than a lead of the second portion.

3. The assembly according to claim 1, further comprising:
a housing; and
an inner housing sleeve arranged within the housing,
wherein the inner housing sleeve comprises at least one first splining member,
wherein the nut member comprises at least one second splining member, and
wherein the nut member is splined to the inner housing sleeve due to mechanical cooperation of the at least one first splining member and the at least one second splining member.

4. The assembly according to claim 3, wherein the at least one first splining member and the at least one second splining member are configured to be disengaged from one another when the nut member passes from the first portion to the second portion, thereby enabling the nut member to perform the tilting movement from the start position into the end position.

5. The assembly according to claim 3, wherein the at least one second splining member comprises an outer shape having a first part and a second part, the first part of the at least one second splining member being inclined relative to the second part of the at least one second splining member.

6. The assembly according to claim 5, wherein:
the second part of the at least one second splining member is configured to be disengaged from the at least one first splining member when the nut member is engaged with the first portion of the thread, and
the second part of the at least one second splining member is oblique with respect to the rotational axis when the nut member is engaged with the first portion of the thread.

7. The assembly according to claim 6, wherein the second part of the at least one second splining member is more oblique relative to the rotational axis when the nut member is engaged with the first portion of the thread than it is when the nut member is engaged with the second portion of the thread.

8. The assembly according to claim 1, further comprising:
a cartridge containing a plurality of doses of a drug; and
a dosing mechanism operable for setting and delivering a dose of the drug from the cartridge, the dosing mechanism comprising a last dose stop mechanism adapted and arranged to inhibit a user from setting a dose of the drug exceeding a remaining amount of drug in the cartridge,
wherein the last dose stop mechanism comprises at least one stop feature provided by the screw member and at least one interaction feature provided by the nut member, the at least one stop feature and the at least one interaction feature being configured to mechanically cooperate with one another when the nut member is in the end position such that further relative rotation of the nut member and the screw member for axially displacing the nut member away from the start position is inhibited.

9. The assembly according to claim 1, wherein the nut member comprises at least one interface feature adapted and arranged to mechanically cooperate with the thread, the interface feature comprising at least a partial thread turn.

10. The assembly according to claim 9, wherein a lead of the at least one interface feature is equal to a lead of the second portion of the thread.

11. The assembly according to claim 9, wherein:
the at least one interface feature comprises a distal face and a proximal face, the distal face and the proximal face being configured to mechanically cooperate with a distal wall of a winding of the thread and a proximal wall of a winding of the thread, respectively,
the distal face and the proximal face are configured to have
a first contact area with a portion of the distal wall of a winding of the second portion of the thread and a portion of the proximal wall of the winding of the second portion of the thread when the nut member mechanically cooperates with the second portion of the thread, and
a second contact area with a portion of the distal wall of a winding of the first portion of the thread and a portion of the proximal wall of the winding of the first portion of the thread when the nut member mechanically cooperates with the first portion of the thread, and
the first contact area is greater than the second contact area.

12. The assembly according to claim 9, wherein, in at least one of the at least two consecutive portions of the thread, the at least one interface feature mechanically cooperates with the thread via distinct and separated contact points.

13. The assembly according to claim 1, further comprising a housing and an inner housing sleeve,
wherein, during the dose setting operation, the screw member is rotated with respect to the nut member and to the inner housing sleeve, the inner housing sleeve being inhibited from rotating due to mechanical cooperation with the housing, and the nut member being inhibited from rotating due to mechanical cooperation with the inner housing sleeve.

14. The assembly according to claim 1, further comprising a housing and an inner housing sleeve,
wherein, during the dose setting operation, the inner housing sleeve and the nut member are rotated with respect to the screw member, the screw member being inhibited from rotating due to mechanical cooperation with the housing, and the nut member being rotated due to mechanical cooperation with the inner housing sleeve.

15. The assembly according to claim 1, further comprising a housing and an inner housing sleeve,
wherein, during a dose delivery operation, each of the screw member, the inner housing sleeve, and the nut member is inhibited from rotating with respect to the housing such that the nut member is inhibited from axially moving with respect to the screw member.

16. The assembly according to claim 1, further comprising a housing and an inner housing sleeve,
wherein, during a dose delivery operation, the screw member and the inner housing sleeve rotate together with respect to the housing due to mechanical cooperation with one another such that the nut member is inhibited from axially moving with respect to the screw member.

17. A drug delivery device comprising:
a cartridge retaining part to a hold a cartridge; and
a dosing mechanism operable to set a dose of drug during a dose setting operation, the dosing mechanism comprising
a screw member comprising a thread, the thread comprising at least two consecutive portions, the at least two consecutive portions having different leads, and
a nut member, wherein the nut member and the screw member are adapted to be rotated with respect to one another about a rotational axis during the dose setting operation of the dosing mechanism, thereby axially displacing the nut member along the screw member from a start position to an end position with respect to the screw member due to mechanical cooperation of the nut member with the thread,
wherein the dosing mechanism is configured such that the nut member performs a tilting movement when the nut member passes from being engaged with a first portion of the at least two consecutive portions to being engaged with a second portion of the at least two consecutive portions, and
wherein when the nut member is engaged with the first portion, the nut member encloses a first angle with an axis transverse to the rotational axis, and when the nut member is engaged with the second portion, the nut member encloses a second angle with the axis transverse to the rotational axis, the second angle being different from the first angle.

18. The drug delivery device according to claim 17, wherein the first portion of the thread is arranged closer to a distal end of the drug delivery device than the second portion, wherein a lead of the first portion is less than a lead of the second portion.

19. A method of operating a drug delivery device, the method comprising:

setting one or more doses of drug by rotating a dose dial grip of the drug delivery device, thereby causing a nut member to be axially displaced along a screw member such that the nut member performs a tilting movement in which the nut member encloses a first angle with an axis transverse to a longitudinal axis of the drug delivery device as the nut member moves along a first portion of at least two consecutive portions of a thread of the screw member and encloses a second angle with the axis transverse to the longitudinal axis as the nut member moves along a second portion of the at least two consecutive portions of the thread of the screw member, the second angle being different from the first angle; and dispensing the one or more doses from a cartridge of the drug delivery device.

20. The method according to claim 19, wherein setting the one or more doses comprises rotating the dose dial grip such that the nut member performs the tilting movement when the nut member moves from a first portion of a thread of the screw member having a first lead to a second portion of the thread having a second lead, the first lead being greater than the second lead.

* * * * *

UNITED STATES PATENT AND TRADEMARK OFFICE
CERTIFICATE OF CORRECTION

PATENT NO.        : 10,668,222 B2
APPLICATION NO.   : 15/534032
DATED             : June 2, 2020
INVENTOR(S)       : Paul Roger Griffin Page 1 of 1

It is certified that error appears in the above-identified patent and that said Letters Patent is hereby corrected as shown below:

In the Claims

In Column 44, Line 44, in Claim 17, after "to" delete "a"

Signed and Sealed this
Twenty-fifth Day of August, 2020

Andrei Iancu
*Director of the United States Patent and Trademark Office*

```
                        SEQUENCE LISTING

<160> NUMBER OF SEQ ID NOS: 40

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 41
<212> TYPE: PRT
<213> ORGANISM: Artificial Sequence
<220> FEATURE:
<223> OTHER INFORMATION: H-(Lys)4-des Pro36, des Pro37 Exendin-4(1-39)-
      NH2

<400> SEQUENCE: 2

Lys Lys Lys Lys His Gly Glu Gly Thr Phe Thr Ser Asp Leu Ser Lys
1               5                   10                  15

Gln Met Glu Glu Glu Ala Val Arg Leu Phe Ile Glu Trp Leu Lys Asn
            20                  25                  30

Gly Gly Pro Ser Ser Gly Ala Pro Ser
        35                  40

<210> SEQ ID NO 3
<211> LENGTH: 42
<212> TYPE: PRT
<213> ORGANISM: Artificial Sequence
<220> FEATURE:
<223> OTHER INFORMATION: H-(Lys)5-des Pro36, des Pro37 Exendin-4(1-39)-
      NH2

<400> SEQUENCE: 3

Lys Lys Lys Lys Lys His Gly Glu Gly Thr Phe Thr Ser Asp Leu Ser
1               5                   10                  15

Lys Gln Met Glu Glu Glu Ala Val Arg Leu Phe Ile Glu Trp Leu Lys
            20                  25                  30
```

```
Asn Gly Gly Pro Ser Ser Gly Ala Pro Ser
         35                  40

<210> SEQ ID NO 4
<211> LENGTH: 38
<212> TYPE: PRT
<213> ORGANISM: Artificial Sequence
<220> FEATURE:
<223> OTHER INFORMATION: des Pro36 Exendin-4(1-39)

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 38
<212> TYPE: PRT
<213> ORGANISM: Artificial Sequence
<220> FEATURE:
<223> OTHER INFORMATION: des Pro36 [Asp28] Exendin-4(1-39)

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: des Pro36 [IsoAsp28] Exendin-4(1-39)
<220> FEATURE:
<221> NAME/KEY: MISC_FEATURE
<222> LOCATION: (28)..(28)
<223> OTHER INFORMATION: x=isoaspartate

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Pro Ser
        35

<210> SEQ ID NO 7
<211> LENGTH: 38
<212> TYPE: PRT
<213> ORGANISM: Artificial Sequence
<220> FEATURE:
<223> OTHER INFORMATION: des Pro36 [Met(O)14, Asp28] Exendin-4(1-39)
<220> FEATURE:
<221> NAME/KEY: MISC_FEATURE
<222> LOCATION: (14)..(14)
<223> OTHER INFORMATION: x=methionine oxide

<400> SEQUENCE: 7

His Gly Glu Gly Thr Phe Thr Ser Asp Leu Ser Lys Gln Xaa Glu Glu
```

```
                1               5                   10                  15
Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 8
<211> LENGTH: 38
<212> TYPE: PRT
<213> ORGANISM: Artificial Sequence
<220> FEATURE:
<223> OTHER INFORMATION: des Pro36 [Met(O)14, IsoAsp28] Exendin-4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (28)..(28)
<223> OTHER INFORMATION: x=isoaspartate

<400> SEQUENCE: 8

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 9
<211> LENGTH: 38
<212> TYPE: PRT
<213> ORGANISM: Artificial Sequence
<220> FEATURE:
<223> OTHER INFORMATION: des Pro36 [Trp(O2)25, Asp28] Exendin-4(1-39)
<220> FEATURE:
<221> NAME/KEY: MISC_FEATURE
<222> LOCATION: (25)..(25)
<223> OTHER INFORMATION: x=tryptophan dioxide

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 10
<211> LENGTH: 38
<212> TYPE: PRT
<213> ORGANISM: Artificial Sequence
<220> FEATURE:
<223> OTHER INFORMATION: des Pro36 [Trp(O2)25, IsoAsp28] Exendin-4(1-39)
<220> FEATURE:
<221> NAME/KEY: MISC_FEATURE
<222> LOCATION: (25)..(25)
<223> OTHER INFORMATION: x=tryptophan dioxide
<220> FEATURE:
<221> NAME/KEY: MISC_FEATURE
<222> LOCATION: (28)..(28)
<223> OTHER INFORMATION: x=isoaspartate

<400> SEQUENCE: 10

His Gly Glu Gly Thr Phe Thr Ser Asp Leu Ser Lys Gln Met Glu Glu
1               5                   10                  15
```

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 11
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, Asp28] Exendin-
      4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan dioxide

<400> SEQUENCE: 11

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser
        35

<210> SEQ ID NO 12
<211> LENGTH: 38
<212> TYPE: PRT
<213> ORGANISM: Artificial Sequence
<220> FEATURE:
<223> OTHER INFORMATION: des Pro36 [Met(O)14 Trp(O2)25, IsoAsp28]
      Exendin-4(1-39)
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan dioxide
<220> FEATURE:
<221> NAME/KEY: MISC_FEATURE
<222> LOCATION: (28)..(28)
<223> OTHER INFORMATION: x=isoapartate

<400> SEQUENCE: 12

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Xaa Gly Gly Pro Ser
            20                  25                  30

Ser Gly Ala Pro Pro Ser
        35

<210> SEQ ID NO 13
<211> LENGTH: 44
<212> TYPE: PRT
<213> ORGANISM: Artificial Sequence
<220> FEATURE:
<223> OTHER INFORMATION: des Pro36 Exendin-4(1-39)-Lys6-NH2

<400> SEQUENCE: 13

His Gly Glu Gly Thr Lys Thr Ser Asp Leu Ser Lys Gln Met Glu Glu
1               5                   10                  15

```
Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```

```
<210> SEQ ID NO 14
<211> LENGTH: 50
<212> TYPE: PRT
<213> ORGANISM: Artificial Sequence
<220> FEATURE:
<223> OTHER INFORMATION: H-(Lys)6-des Pro36 [Asp28] Exendin-4(1-39)-
      Lys6-NH2

<400> SEQUENCE: 14

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50
```

```
<210> SEQ ID NO 15
<211> LENGTH: 38
<212> TYPE: PRT
<213> ORGANISM: Artificial Sequence
<220> FEATURE:
<223> OTHER INFORMATION: des Asp28 Pro36, Pro37, Pro38Exendin-4(1-39)-
      NH2

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gly Gly Pro Ser Ser
            20                  25                  30

Gly Ala Pro Pro Pro Ser
        35
```

```
<210> SEQ ID NO 16
<211> LENGTH: 44
<212> TYPE: PRT
<213> ORGANISM: Artificial Sequence
<220> FEATURE:
<223> OTHER INFORMATION: H-(Lys)6-des Pro36, Pro38 [Asp28] Exendin-4(1-
      39)-NH2

<400> SEQUENCE: 16

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser
        35                  40
```

```
<210> SEQ ID NO 17
<211> LENGTH: 44
<212> TYPE: PRT
<213> ORGANISM: Artificial Sequence
<220> FEATURE:
<223> OTHER INFORMATION: H-Asn-(Glu)5des Pro36, Pro37, Pro38 [Asp28]
      Exendin-4(1-39)-NH2

<400> SEQUENCE: 17
```

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Pro Pro Ser
            35                  40

<210> SEQ ID NO 18
<211> LENGTH: 44
<212> TYPE: PRT
<213> ORGANISM: Artificial Sequence
<220> FEATURE:
<223> OTHER INFORMATION: des Pro36, Pro37, Pro38 [Asp28] Exendin-4(1-
      39)-(Lys)6-NH2

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
                20                  25                  30

Ser Gly Ala Pro Pro Ser Lys Lys Lys Lys Lys Lys
            35                  40

<210> SEQ ID NO 19
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Asp28]
      Exendin-4(1-39)-(Lys)6-NH2

<400> SEQUENCE: 19

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Pro Pro Ser Lys Lys Lys Lys
            35                  40                  45

Lys Lys
    50

<210> SEQ ID NO 20
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Asp28]
      Exendin-4(1-39)-(Lys)6-NH2

<400> SEQUENCE: 20

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Pro Pro Ser Lys Lys Lys Lys
            35                  40                  45

Lys Lys
    50

<210> SEQ ID NO 21
<211> LENGTH: 50

```
<212> TYPE: PRT
<213> ORGANISM: Artificial Sequence
<220> FEATURE:
<223> OTHER INFORMATION: H-(Lys)6-des Pro36 [Trp(O2)25, Asp28] Exendin-
      4(1-39)-Lys6-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 21

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 22
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Trp(O2)25]
      Exendin-4(1-39)-NH2
<220> FEATURE:
<221> NAME/KEY: MISC_FEATURE
<222> LOCATION: (25)..(25)
<223> OTHER INFORMATION: x=tryptophan dioxide

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Gly Gly Pro Ser Ser
            20                  25                  30

Gly Ala Pro Pro Pro Ser
        35

<210> SEQ ID NO 23
<211> LENGTH: 44
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 23

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 24
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38
```

[Trp(O2)25, Asp28] Exendin-4(1-39)-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 24

Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser
        35                  40

<210> SEQ ID NO 25
<211> LENGTH: 44
<212> TYPE: PRT
<213> ORGANISM: Artificial Sequence
<220> FEATURE:
<223> OTHER INFORMATION: des Pro36, Pro37, Pro38 [Trp(O2)25, Asp28]
      Exendin-4(1-39)-(Lys)6-NH2
<220> FEATURE:
<221> NAME/KEY: MISC_FEATURE
<222> LOCATION: (25)..(25)
<223> OTHER INFORMATION: x=tryptophan dioxide

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Xaa Leu Lys Asp Gly Gly Pro Ser
            20                  25                  30

Ser Gly Ala Pro Pro Ser Lys Lys Lys Lys Lys Lys
        35                  40

<210> SEQ ID NO 26
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Trp(O2)25,
      Asp28] Exendin-4(1-39)-(Lys)6-NH2
<220> FEATURE:
<221> NAME/KEY: MISC_FEATURE
<222> LOCATION: (31)..(31)
<223> OTHER INFORMATION: x=tryptophan dioxide

<400> SEQUENCE: 26

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 27
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38
      [Trp(O2)25, Asp28] Exendin-4(1-39)-(Lys)6-NH2
<220> FEATURE:
<221> NAME/KEY: MISC_FEATURE
<222> LOCATION: (31)..(31)

<223> OTHER INFORMATION: x=tryptophan dioxide

<400> SEQUENCE: 27

Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 28
<211> LENGTH: 50
<212> TYPE: PRT
<213> ORGANISM: Artificial Sequence
<220> FEATURE:
<223> OTHER INFORMATION: H-(Lys)6-des Pro36 [Met(O)14, Asp28] Exendin-
      4(1-39)-Lys6-NH2
<220> FEATURE:
<221> NAME/KEY: MISC_FEATURE
<222> LOCATION: (20)..(20)
<223> OTHER INFORMATION: x=methionine oxide

<400> SEQUENCE: 28

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 29
<211> LENGTH: 38
<212> TYPE: PRT
<213> ORGANISM: Artificial Sequence
<220> FEATURE:
<223> OTHER INFORMATION: des Met(O)14 Asp28 Pro36, Pro37, Pro38 Exendin-
      4(1-39)-NH2

<400> SEQUENCE: 29

His Gly Glu Gly Thr Phe Thr Ser Asp Leu Ser Lys Gln Glu Glu Glu
1               5                   10                  15

Ala Val Arg Leu Phe Ile Glu Trp Leu Lys Asp Gly Gly Pro Ser Ser
            20                  25                  30

Gly Ala Pro Pro Pro Ser
        35

<210> SEQ ID NO 30
<211> LENGTH: 44
<212> TYPE: PRT
<213> ORGANISM: Artificial Sequence
<220> FEATURE:
<223> OTHER INFORMATION: H-(Lys)6-desPro36, Pro37, Pro38 [Met(O)14,
      Asp28] Exendin-4(1-39)-NH2
<220> FEATURE:
<221> NAME/KEY: MISC_FEATURE
<222> LOCATION: (20)..(20)
<223> OTHER INFORMATION: x=methionine oxide

<400> SEQUENCE: 30

Lys Lys Lys Lys Lys Lys His Gly Glu Gly Thr Phe Thr Ser Asp Leu

```
                1               5                   10                  15
Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
            35                  40

<210> SEQ ID NO 31
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Asp28] Exendin-4(1-39)-NH2
<220> FEATURE:
<221> NAME/KEY: MISC_FEATURE
<222> LOCATION: (20)..(20)
<223> OTHER INFORMATION: x=methionine oxide

<400> SEQUENCE: 31

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser
            35                  40

<210> SEQ ID NO 32
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Asp28]
      Exendin-4(1-39)-(Lys)6-NH2
<220> FEATURE:
<221> NAME/KEY: MISC_FEATURE
<222> LOCATION: (14)..(14)
<223> OTHER INFORMATION: x=methionine oxide

<400> SEQUENCE: 32

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 33
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide

<400> SEQUENCE: 33

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
            35                  40                  45
```

```
Lys Lys
    50

<210> SEQ ID NO 34
<211> LENGTH: 50
<212> TYPE: PRT
<213> ORGANISM: Artificial Sequence
<220> FEATURE:
<223> OTHER INFORMATION: H-Asn-(Glu)5 des Pro36, Pro37, Pro38 [Met(O)14,
      Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide

<400> SEQUENCE: 34

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 35
<211> LENGTH: 50
<212> TYPE: PRT
<213> ORGANISM: Artificial Sequence
<220> FEATURE:
<223> OTHER INFORMATION: H-Lys6-des Pro36 [Met(O)14, Trp(O2)25, Asp28]
      Exendin-4(1-39)-Lys6-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan dioxide

<400> SEQUENCE: 35

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 36
<211> LENGTH: 38
<212> TYPE: PRT
<213> ORGANISM: Artificial Sequence
<220> FEATURE:
<223> OTHER INFORMATION: H-des Asp28 Pro36, Pro37, Pro38 [Met(O)14,
      Trp(O2)25] Exendin-4(1-39)-NH2
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan oxide
```

```
<400> SEQUENCE: 36

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Gly Gly Pro Ser Ser
                20                  25                  30

Gly Ala Pro Pro Pro Ser
            35

<210> SEQ ID NO 37
<211> LENGTH: 44
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan oxide

<400> SEQUENCE: 37

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
                20                  25                  30

Lys Asp Gly Gly Pro Ser Ser Gly Ala Pro Pro Ser
            35                  40

<210> SEQ ID NO 38
<211> LENGTH: 44
<212> TYPE: PRT
<213> ORGANISM: Artificial Sequence
<220> FEATURE:
<223> OTHER INFORMATION: des Pro36, Pro37, Pro38 [Met(O)14, Trp(O2)25,
      Asp28] Exendin-4(1-39)-(Lys)6-NH2
<220> FEATURE:
<221> NAME/KEY: MISC_FEATURE
<222> LOCATION: (14)..(14)
<223> OTHER INFORMATION: x=methionine oxide
<220> FEATURE:
<221> NAME/KEY: MISC_FEATURE
<222> LOCATION: (25)..(25)
<223> OTHER INFORMATION: x=tryptophan oxide

<400> SEQUENCE: 38

His Gly Glu Gly Thr Phe Thr Ser Asp Leu Ser Lys Gln Xaa Glu Glu
1               5                   10                  15

Glu Ala Val Arg Leu Phe Ile Glu Xaa Leu Lys Asp Gly Gly Pro Ser
                20                  25                  30

Ser Gly Ala Pro Pro Ser Lys Lys Lys Lys Lys Lys
            35                  40

<210> SEQ ID NO 39
<211> LENGTH: 50
<212> TYPE: PRT
<213> ORGANISM: Artificial Sequence
<220> FEATURE:
<223> OTHER INFORMATION: H-(Lys)6-des Pro36, Pro37, Pro38 [Met(O)14,
      Trp(O2)25, Asp28] Exendin-4(S1-39)-(Lys)6-NH2
<220> FEATURE:
<221> NAME/KEY: MISC_FEATURE
<222> LOCATION: (20)..(20)
<223> OTHER INFORMATION: x=methionine oxide
```

```
<220> FEATURE:
<221> NAME/KEY: MISC_FEATURE
<222> LOCATION: (31)..(31)
<223> OTHER INFORMATION: x=tryptophan oxide

<400> SEQUENCE: 39

Lys Lys Lys Lys Lys Lys His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 40
<211> LENGTH: 50
<212> TYPE: PRT
<213> ORGANISM: Artificial Sequence
<220> FEATURE:
<223> OTHER INFORMATION: H-Asn-(Glu)5-des Pro36, Pro37, Pro38 [Met(O)14,
      Trp(O2)25, Asp28] Exendin-4(1-39)-(Lys)6-NH2
<220> FEATURE:
<221> NAME/KEY: MISC_FEATURE
<222> LOCATION: (20)..(20)
<223> OTHER INFORMATION: x=methionine oxide
<220> FEATURE:
<221> NAME/KEY: MISC_FEATURE
<222> LOCATION: (31)..(31)
<223> OTHER INFORMATION: x=tryptophan oxide

<400> SEQUENCE: 40

Asn Glu Glu Glu Glu Glu His Gly Glu Gly Thr Phe Thr Ser Asp Leu
1               5                   10                  15

Ser Lys Gln Xaa Glu Glu Glu Ala Val Arg Leu Phe Ile Glu Xaa Leu
            20                  25                  30

Lys Asp Gly Gly Pro Ser Ser Gly Ala Pro Pro Ser Lys Lys Lys Lys
        35                  40                  45

Lys Lys
    50
```